United States Patent [19]

Castor et al.

[11]  4,132,743

[45]  Jan. 2, 1979

[54] REDUCTION OF METAL SURFACE-INITIATED CRACKING IN DEHYDROGENATION REACTORS

[75] Inventors: William M. Castor, Richwood; Barbara S. Taylor, Lake Jackson, both of Tex.

[73] Assignee: The Dow Chemical Company, Midland, Mich.

[21] Appl. No.: 886,198

[22] Filed: Mar. 13, 1978

[51] Int. Cl.² ............................................. C07C 15/00
[52] U.S. Cl. ............................................... 260/669 R
[58] Field of Search ................. 23/252 A; 260/669 R; 208/48 R

[56] References Cited

U.S. PATENT DOCUMENTS

| | | | |
|---|---|---|---|
| 2,168,840 | 8/1939 | Groll | 260/669 R |
| 3,787,188 | 1/1974 | Lyon | 260/669 R |
| 4,008,180 | 2/1977 | Rausch | 260/669 R |

Primary Examiner—Delbert E. Gantz
Assistant Examiner—Joseph A. Boska
Attorney, Agent, or Firm—D. H. Thurston; G. R. Baker

[57] ABSTRACT

Low yield thermal cracking of a hydrocarbon such as ethylbenzene caused by contact with active metal surfaces in a catalytic dehydrogenation reactor is reduced by coating the metal surfaces, particularly those in the feed inlet end, with a thin layer of an inactivating metal or metal compound, such as $V_2O_5$, preferably in an inert ceramic medium.

13 Claims, 1 Drawing Figure

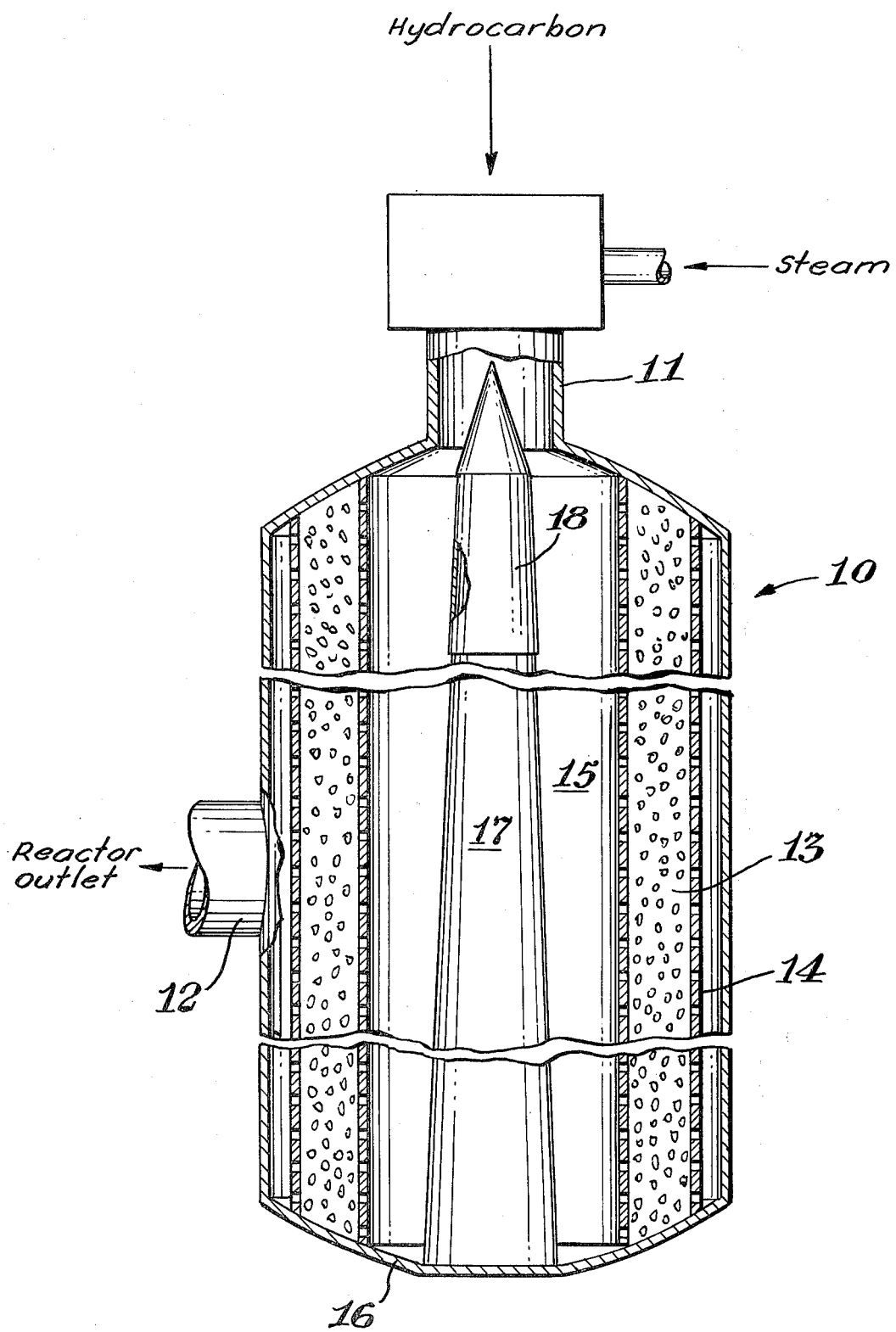

REDUCTION OF METAL SURFACE-INITIATED CRACKING IN DEHYDROGENATION REACTORS

BACKGROUND OF THE INVENTION

The present invention relates to an improvement in a catalytic dehydrogenation process and in a reactor used therein. It relates particularly to a method whereby the amount of undesirable nonselective cracking promoted by active metal surfaces in a catalytic dehydrogenation reactor can be substantially reduced.

In the catalytic dehydrogenation of a hydrocarbon having an alkyl moiety to a corresponding alkenyl compound, for example, the conversion of ethylbenzene to styrene, ethyltoluene to vinyltoluene, and butene to butadiene, there is also a certain amount of cracking which results both from exposure of the hydrocarbon feed to elevated process temperatures whereby some thermal cracking takes place and from contact of the hydrocarbon with hot metal surfaces within the reactor prior to contact with the catalyst where those metal surfaces catalyze a low yield conversion or decomposition of the feed. U.S. Pat. No. 3,474,153 documents the use of preferred metals of construction typically low in nickel content for minimizing such yield loss at reaction conditions. Both the strictly thermal cracking and the cracking which is promoted by an active metal surface can begin at a temperature as low as 450° C and since catalytic dehydrogenation process temperatures range generally from about 550° C to about 650° C, it is obvious that loss of hydrocarbon feed to these destructive side reactions can be significant. Certain stainless steel alloys and some other such corrosion and heat resistant alloys commonly used in constructing catalytic dehydrogenation reactors actively promote nonselective cracking and alloys containing a high proportion of nickel are particularly bad in this respect. Both of these side reactions can detract substantially from the ultimate yield of the desired olefinic product.

The first of these destructive side reactions can be minimized by reducing the residence time of the hydrocarbon feed within the void space in a cracking reactor so that the feed contacts the catalyst more rapidly after reaching a cracking temperature. This can be accomplished by changes in reactor design. For example, in the newer radial dehydrogenation reactors, the feed is introduced into the central void of a hollow cylindrical catalyst bed and it passes from there outwardly through the surrounding cylindrical body of catalyst to the outlet. In the copending application of Sutherland, Ser. No. 760,896, filed Jan. 21, 1977, in the hands of a common assignee, the volume of the central void in such a reactor, and consequently the residence time of the incoming feed within that void is reduced either by shaping the catalyst bed into a truncated hollow cone with the larger end toward the feed inlet or by introducing a generally conically-shaped filler into the central void. In either case, the residence time of the feed within the central void is reduced without changing the contact time in the catalyst bed. The total metal surface which the feed has to contact before reaching the catalyst bed is not greatly reduced by the first of these expedients and the metal surface area is substantially increased by the second. Thus, the problem of nonselective conversion caused by an active metal surface remains.

SUMMARY OF THE INVENTION

It has now been found that in a process for catalytically dehydrogenating a hydrocarbon having an alkyl moiety to a corresponding alkenyl compound wherein a gaseous mixture of said hydrocarbon and an inert diluent is fed into a void enclosed by metal walls and containing a solid dehydrogenation catalyst at an elevated temperature and wherein said hydrocarbon undergoes a significant amount of nonselective cracking upon contact with said metal walls at the elevated temperature, the nonselective cracking caused by contact with the metal walls can be significantly inhibited by coating at least a portion of said walls with a substantially continuous film of about 5–50 mils thickness of at least one of $V_2O_5$, vanadium diboride, vanadium metal, $Cr_2O_3$, $TeO_2$, $ZrO_2$, or $TiO_2$. Preferably, the film consists of a solid solution or suspension of one or more of the above in an inert ceramic medium.

DESCRIPTION OF THE DRAWING

FIG. 1 is a side section of a catalytic dehydrogenation reactor, 10, of radial design having an inlet 11, where hydrocarbon feed and steam diluent are mixed, an outlet, 12, a cylindrical body of catalyst, 13, held in place by a basket-like structure, 14, a central void or distributor zone, 15, directly below the inlet, 11, and defined by the inner surface of the catalyst basket, 14, and by the bottom, 16, of the reactor, 10. A generally conical filler or deflector, 17, is located within the central void, 15, with a passivating film, 18, of the invention coating at least the inlet end of the filler, 17.

DETAILED DESCRIPTION OF THE INVENTION

The FIGURE illustrates only one minimum way in which the present invention can be used to advantage. For example, the filler, 17, can be paraboloidal in shape to reduce even more the residence time of the feed within the void, 15, and its entire surface can be coated with the passivating film, 18. Also, the passivating film can be applied to other surfaces within or contiguous with the reactor to obtain additional advantage, for example, the inner surface of the inlet, 11, the inner surface of the reactor outlet, 12, and the inner surface of the catalyst basket, 14, in short, any or all of such surfaces where hydrocarbon feed or product comes into contact with metal at elevated temperature. Alternatively, inner surfaces of reactors constructed according to different designs or lacking the central filler, 17, can be coated to advantage with the passivating film.

In a preferred embodiment, the passivating film is composed of one or more of the above named passivating agents suspended or dissolved in solid solution in an inert ceramic medium which acts as an adhesive base to make a continuous fused film firmly bonded to the metal surface. The ceramic medium can be chromium monoxide, CrO, which is used particularly as a base in coating by plasma arc spraying. The ceramic medium can also be a glass or glaze based essentially on silica, silicate, or borosilicate and having a suitable coefficient of thermal expansion and a softening point substantially above temperatures reached during the dehydrogenation process. Both raw and fritted ceramic glazes having these properties are operable in the present invention. Such glazes typically are composed of one or more silica-containing substances such as silica clay, feldspar, or a borosilicate frit as main ingredients plus smaller amounts of lime, magnesia, or other metal compounds as modifying additives. Such a glaze plus the desired passivating agent is readily applied to the metal reactor surface by conventional techniques, for example, as an aqueous slurry or slip coating which is dried and then fused or sintered in place.

At least about two percent of the passivating agent based on the weight of ceramic base is required and preferably about 5-10 percent of passivating agent is used to obtain effective passivation of an active metal surface. Much larger proportions of passivating agent can be employed, for example, as much as 50-75 percent or more of the weight of ceramic base, but these larger proportions ordinarily provide little if any added advantage and poor bonding to the metal surface often results.

Alternatively, of course, if the passivating agent itself can be adhered to the metal surface to form a film which is sufficiently durable under dehydrogenation process conditions, it can be used without any ceramic base.

An average film thickness of at least about 5 mils (0.127 mm) is required to make a reasonably continuous film and a film thickness of 10-20 mils is preferred for substantial elimination of micropores and a fully effective coating. As the film thickness exceeds 50 mils, there is an excessive amount of cracking and flaking off caused mainly by temperature changes.

The film can be applied and formed on the metal surface by any of several known methods. Effective films are conveniently formed on the surface by flame spraying or plasma-arc spraying of the coating composition. The passivating agent can also be mixed with a fluid ceramic medium as previously described, the mixture coated on a surface, and the coating then sintered or melted to form a film by calcining at a temperature of 1000° C or above.

The passivating film composition of this invention are not only effective, but they are also durable and long-lasting under dehydrogenating conditions. Films applied to inner surfaces of catalytic dehydrogenation reactors were found to be intact and fully effective when those reactors were shut down and examined after operating for several months under commercial process conditions.

EXAMPLE 1

Comparative thermal ethylbenzene cracking experiments were run by passing 35 ml/hr of ethylbenzene and 30 ml/hr of water as the mixed vapors through one inch diameter tubes or pipes of various materials at different temperatures. A 7-inch section of each tube was packed with quarter inch porcelain berl saddles and this section was maintained at the indicated temperature for running times of several hours. Conversion of ethylbenzene to other products and percent yield of styrene from the converted ethylbenzene were determined by measuring and analyzing the effluent organic product. These results are listed in Table I.

TABLE I

| Tube Material | Temp. °C | % Conversion Ethylbenzene | % Yield Styrene |
|---|---|---|---|
| 316 ss | 630 | 2.7 | 73.9 |
|  | 650 | 7.7 | 69.5 |
|  | 667 | 14.2 | 69.3 |
|  | 690 | 27.0 | 66.2 |
| Incalloy 800 | 629 | 3.0 | 74.3 |
|  | 649 | 6.8 | 71.7 |
|  | 670 | 15.0 | 67.8 |
|  | 690 | 26.8 | 65.3 |
| Inconel 601 | 626 | 2.6 | 70.4 |
|  | 651 | 6.7 | 68.2 |
|  | 673 | 18.6 | 61.3 |
|  | 690* | 37.1 | 39.1 |

*Reactor tube was choked with carbon after 3 hours running time.

These data show that the materials of construction can significantly affect the apparent thermal conversion at a given set of operating conditions. In general, as the nickel content of a metal increases, the thermal activity of the metal also increases.

EXAMPLE 2

In order to study the effect of a coating, high surface area metal mesh plugs were put in a controlled temperature zone in a high silica glass tube and mixed ethylbenzene vapor and steam was passed through as described in Example 1. A run made using the empty high silica glass tube was used as a standard, assuming that there was negligible surface activity and that the conversion observed in that tube was caused entirely by thermal cracking in the bulk gas phase. All runs were made at 690° C.

TABLE II

| Test Material | % Conversion of Ethylbenzene | | | % of Total Conversion Due to Surface |
|---|---|---|---|---|
|  | Total | Thermal | Surface |  |
| High Silica Glass Tube | 24.8 | 24.8 | 0[1] | 0[1] |
| 316 ss | 30.6 | 24.8[1] | 5.8 | 18.8 |
| Inconel 601 Coated[2] | 32.5 | 24.8[1] | 7.7 | 23.7 |
| 316 ss | 27.7 | 24.8[1] | 2.9 | 10.4 |

[1]Assumed.
[2]Plasma-arc sprayed with a 5 percent $V_2O_5$-95 percent CrO mixture to a thickness of 10-15 mils. About 5-7 percent of the $V_2O_5$ was converted to V metal in the coating process.

Results similar to those shown for the high silica glass reactor tube are obtained when a tube of 446 stainless steel (no nickel content) is used.

EXAMPLES 3-14

In a manner similar to that described in Example 2, 1 × 6 inch plugs of 316 stainless steel mesh coated with various substances were tested for the dehydrogenation of ethylbenzene in the presence of steam. Mesh coated with a clay-based ceramic glaze was prepared by adding the desired amount of passivating agent to the glaze slurry (Duncan GL 617), drying mesh coated with the slurry, and then calcining at 1000° C for 2 hours. Duncan GL 617 (Duncan Ceramics Products, Inc.) is a commercially available fritted glaze which typically contains silica gel, alumina, lead bisilicate, and some bentonite clay in a water suspension. A typical composition contains 2.0 moles of $SiO_2$, 0.1 mole of $Al_2O_3$, and 1.0 mole of PbO in water. For purpose of comparison, blank runs were made with the reactor tube containing the uncoated metal mesh, mesh coated only with Duncan GL 617 ceramic glaze and mesh which had been plasma-arc sprayed with CrO. Other runs were made using the metal mesh which had been coated, flame sprayed or plasma-arc sprayed with a passivating agent in an inert ceramic medium. All three coating methods provided continuous coatings substantially free of pinholes. The thickness of the coating on the stainless steel mesh in all cases was about 10-15 mils. The coated mesh plug was inserted into a one-inch Incalloy 800 pipe reactor which was heated and maintained at 668°-691° C. Ethylbenzene and water in a 1:2 weight ratio were vaporized and the mixed vapors were passed through the reactor at about atmospheric pressure. The conversion of ethylbenzene and yield of styrene were determined as before by analysis of the effluent product after one hour of running under these conditions.

The total surface conversion rates in percent per square meter per second were calculated from the void volume of the reactor contents, the surface area as measured by nitrogen adsorption, and the analyses of the effluent products. All of these results are listed in Table III.

TABLE III

| Ex. No. | Reactor Packing | % Conv. | % Yield | % Conv./m²/sec. |
|---|---|---|---|---|
| 3 | uncoated mesh | 33.6 | 63.9 | 9.7 |
| 4 | glaze-coated mesh | 32.9 | 66.7 | 9.4 |
| 5 | CrO-coated mesh | 31.9 | 69.2 | 9.0 |
| 6 | mesh + 5% $V_2O_5$ in glaze | 26.5 | 68.7 | 5.4 |
| 7 | mesh + 5% $VB_2$ in glaze | 31.1 | 65.8 | 6.7 |
| 8 | mesh + 5% V metal in glaze | 28.2 | 67.8 | 5.2 |
| 9 | mesh + 5% $V_2O_5$[1] in CrO | 26.6 | 70.3 | 5.6 |
| 10 | mesh + 100% $V_2O_5$ (flame sprayed) | 27.7 | 72.3 | 7.0 |
| 11 | mesh + 5% $TeO_2$ in glaze | 27.9 | 67.9 | 5.2 |
| 12 | mesh + 5% $ZnO_2$ in glaze | 26.8 | 68.1 | 5.1 |
| 13 | mesh + 5% $Cr_2O_3$ in glaze | 25.6 | 69.2 | 5.6 |
| 14 | mesh + 5% $TiO_2$ in glaze | 28.1 | 67.8 | 5.9 |

[1] About 5-7 percent of the $V_2O_5$ was converted to vanadium metal in the plasma arc coating process.

Results similar to those reported above for the steam dehydrogenation of ethylbenzene to styrene are obtained when the same procedures are applied to the dehydrogenation of other hydrocarbons, for example, in the dehydrogenation of butene to butadiene, the dehydrogenation of ethyltoluene to vinyltoluene, and the dehydrogenation of isopropylbenzene to α-methylstyrene. Such dehydrogenations are ordinarily run using an inert diluent for the hydrocarbon feed, which diluent may be nitrogen, carbon dioxide, or methane but which is most commonly steam.

We claim:

1. In the process for catalytically dehydrogenating a hydrocarbon having an alkyl moiety to a corresponding alkenyl compound wherein a gaseous mixture of said hydrocarbon and an inert diluent is fed at an elevated temperature into a void enclosed by metal walls and containing a solid dehydrogenation catalyst and wherein said hydrocarbon undergoes a significant amount of nonselective cracking upon contact with said metal walls at the elevated temperature, the improvement comprising coating at least a portion of said metal walls with a substantially continuous film of a passivating agent selected from the group consisting of $Cr_2O_3$, $V_2O_5$, vanadium boride, vanadium metal, $TeO_2$, $ZrO_2$, $TiO_2$, or a mixture thereof, thereby substantially reducing said nonselective cracking.

2. The process of claim 1 wherein the film has an average thickness of about 5-50 mils.

3. The process of claim 2 wherein the hydrocarbon is ethylbenzene.

4. The process of claim 1 wherein the film consists essentially of an inert ceramic medium containing at least about two percent of its weight of passivating agent, said ceramic medium being CrO or a ceramic glaze.

5. The process of claim 4 wherein the film is composed of CrO plus at least about 2 percent of its weight of $V_2O_5$.

6. The process of claim 4 wherein the film is composed of a ceramic glaze plus at least about 2 percent of its weight of $V_2O_5$.

7. The process of claim 4 wherein the film is composed of a ceramic glaze plus at least about 2 percent of its weight of vanadium boride.

8. The process of claim 4 wherein the film is composed of a ceramic glaze plus at least about 2 percent of its weight of $ZrO_2$.

9. The process of claim 4 wherein the film is composed of a ceramic glaze plus at least about 2 percent of its weight of $TiO_2$.

10. The process of claim 4 wherein the film is composed of a ceramic glaze plus at least about 2 percent of its weight of $TeO_2$.

11. The process of claim 4 wherein the film is composed of a ceramic glaze plus at least about 2 percent of its weight of $Cr_2O_3$.

12. The process of claim 4 wherein the film is composed of a ceramic glaze plus at least about 2 percent of its weight of vanadium metal.

13. The process of claim 1 wherein the coating consists essentially of $V_2O_5$.

* * * * *